(12) United States Patent
Harada

(10) Patent No.: US 12,213,651 B2
(45) Date of Patent: Feb. 4, 2025

(54) IMAGING SYSTEM AND ENDOSCOPE

(71) Applicant: OLYMPUS CORPORATION, Hachioji (JP)

(72) Inventor: Yasunari Harada, Ebina (JP)

(73) Assignee: OLYMPUS CORPORATION, Tokyo (JP)

( * ) Notice: Subject to any disclaimer, the term of this patent is extended or adjusted under 35 U.S.C. 154(b) by 398 days.

(21) Appl. No.: 17/852,503

(22) Filed: Jun. 29, 2022

(65) Prior Publication Data
US 2022/0322923 A1 Oct. 13, 2022

Related U.S. Application Data

(63) Continuation of application No. PCT/JP2020/000463, filed on Jan. 9, 2020.

(51) Int. Cl.
| | |
|---|---|
| *A61B 1/045* | (2006.01) |
| *A61B 1/00* | (2006.01) |
| *H04N 23/50* | (2023.01) |
| *H04N 23/60* | (2023.01) |
| *H04N 25/75* | (2023.01) |

(52) U.S. Cl.
CPC .......... *A61B 1/045* (2013.01); *A61B 1/00006* (2013.01); *H04N 23/555* (2023.01); *H04N 23/60* (2023.01); *H04N 23/665* (2023.01); *H04N 25/75* (2023.01)

(58) Field of Classification Search
CPC ...... H04N 25/7795; H04N 25/75; H04N 5/04; H04N 7/18; H04N 23/665; H04N 23/60
See application file for complete search history.

(56) References Cited

U.S. PATENT DOCUMENTS

| | | | |
|---|---|---|---|
| 2004/0073086 A1* | 4/2004 | Abe | H04N 23/65 600/109 |
| 2020/0281452 A1* | 9/2020 | Moon | A61B 1/0655 |

FOREIGN PATENT DOCUMENTS

| | | |
|---|---|---|
| EP | 0 069 561 A1 | 1/1983 |
| JP | 58-6635 A | 1/1983 |
| JP | 2001-331141 A | 11/2001 |
| JP | 2004-49250 A | 2/2004 |
| JP | 2004-49770 A | 2/2004 |
| JP | 2011-36414 A | 2/2011 |
| WO | 2019/193937 A1 | 10/2019 |

OTHER PUBLICATIONS

International Search Report dated Apr. 7, 2020, issued in counterpart International Application No. PCT/JP2020/000463, w/English translation (4 pages).

* cited by examiner

*Primary Examiner* — Kathleen V Nguyen
(74) *Attorney, Agent, or Firm* — WHDA, LLP

(57) ABSTRACT

In an imaging system, a video output circuit is configured to convert an analog video signal into digital data and output serial data including the digital data to a signal line on the basis of a serial clock having a higher frequency than a frequency of the camera clock. A camera-clock generation circuit is configured to generate the camera clock synchronized with the system clock output to the signal line. A serial-clock generation circuit is configured to generate the serial clock synchronized with the system clock output to the signal line. A system-clock output circuit is configured to output the system clock to the signal line in a blanking period.

10 Claims, 11 Drawing Sheets

IMAGING SYSTEM AND ENDOSCOPE

The present application is a continuation application based on International Patent Application No. PCT/JP2020/000463 filed on Jan. 9, 2020, the content of which is incorporated herein by reference.

BACKGROUND OF THE INVENTION

Field of the Invention

The present invention relates to an imaging system and an endoscope.

Description of Related Art

An imaging system including two units is disclosed in Japanese Unexamined Patent Application. First Publication No. 2011-036414. This imaging system includes a camera unit (insertion unit) and a control unit (processor). The camera unit includes an imager constituted by a charge-coupled device (CCD), an analog-to-digital (AD) converter, and a serializer. The imager generates an analog video signal. The AD convener converts the analog video signal into parallel digital data. The serializer converts the digital data into serial data. The camera unit and the control unit are connected to each other by a signal line for transmitting the analog video signal.

A timing generator configured to generate a clock supplied to the AD convener is disposed on the control unit side. The clock is transmitted to the camera unit.

SUMMARY OF THE INVENTION

According to a first aspect of the present invention, an imaging system includes a camera unit and a control unit that is configured to operate on the basis of a system clock and is connected to the camera unit by a signal line that transmits serial data and the system clock. The camera unit includes an imager, a video output circuit, a camera-clock generation circuit, and a serial-clock generation circuit. The imager is configured to generate an analog video signal on the basis of a camera clock. The video output circuit is configured to convert the analog video signal into digital data and output the serial data including the digital data to the signal line on the basis of a serial clock having a higher frequency than a frequency of the camera clock. The camera-clock generation circuit is configured to generate the camera clock synchronized with the system clock output to the signal line. The serial-clock generation circuit is configured to generate the serial clock synchronized with the system clock output to the signal line. The control unit includes a video reception circuit and a system-clock output circuit. The video reception circuit is electrically connected to the signal line and is configured to receive the serial data. The system-clock output circuit is configured to output the system clock to the signal line in a blanking period during which output of the serial data to the signal line is stopped.

According to a second aspect of the present invention, in the first aspect, the video output circuit may include an analog-to-digital conversion circuit and a serializer. The analog-to-digital conversion circuit may be configured to convert the analog video signal into the digital data including a plurality of parallel bits. The serializer may be configured to convert the digital data into the serial data and output the serial data to the signal line at a timing synchronized with the serial clock.

According to a third aspect of the present invention, in the first aspect, the video output circuit may include an analog-to-digital conversion circuit that is configured to convert the analog video signal into the serial data and output the serial data to the signal line at a timing synchronized with the serial clock.

According to a fourth aspect of the present invention, in the first aspect, the camera-clock generation circuit may be configured to generate the camera clock by dividing a frequency of the serial clock.

According to a fifth aspect of the present invention, in the first aspect, the serial data may include two or more pieces of high level data and two or more pieces of low level data. The video output circuit may include an encoding circuit configured to encode the serial data such that the sum of lengths of periods occupied by the two or more pieces of high level data output to the signal line is almost the same as the sum of lengths of periods occupied by the two or more pieces of low level data output to the signal line.

According to a sixth aspect of the present invention, in the first aspect, the video output circuit may include a three-state buffer configured to turn into any one of a high-level state, a low-level state, and a high-impedance state. The state of the three-state buffer may switch between the high-level state, the low-level state, and the high-impedance state. The three-state buffer may be configured to output the serial data to the signal line by turning into the high-level state or the low-level state and turn into the high-impedance state in the blanking period.

According to a seventh aspect of the present invention, in the first aspect, the system-clock output circuit may be configured to output the system clock including a negative voltage to the signal line. The camera unit may further include a capacitor that is configured to hold the negative voltage and output the negative voltage to the imager.

According to an eighth aspect of the present invention, in the seventh aspect, the system-clock output circuit may be configured to output the system clock alternately including a positive voltage and the negative voltage to the signal line. The camera unit may further include a switch and a control circuit. The switch may be capable of switching between an ON state and an OFF state and may be electrically connected to the signal line and the capacitor. The control circuit may be configured to set a state of the switch to the ON state when the negative voltage is output to the signal line and set the state of the switch to the OFF state when the positive voltage is output to the signal line.

According to a ninth aspect of the present invention, in the seventh aspect, the system-clock output circuit may be configured to output the system clock including the negative voltage lower than a design voltage designed for the imager such that the negative voltage input to the capacitor almost matches the design voltage.

According to a tenth aspect of the present invention, an endoscope is connected to a control unit by a signal line that transmits serial data and a system clock. The endoscope includes an imager, a video output circuit, a camera-clock generation circuit, and a serial-clock generation circuit. The imager is configured to generate an analog video signal on the basis of a camera clock. The video output circuit is configured to convert the analog video signal into digital data and output the serial data including the digital data to the signal line on the basis of a serial clock having a higher frequency than a frequency of the camera clock. The camera-clock generation circuit is configured to generate the camera clock synchronized with the system clock output to the signal line in a blanking period during which output of the serial data to the signal line is stopped. The serial-clock generation circuit is configured to generate the serial clock synchronized with the system clock output to the signal line.

DETAILED DESCRIPTION OF THE INVENTION

Hereinafter, embodiments of the present invention will be described with reference to the drawings. Each of the embodiments will be described in detail by using an endoscope system as an example of an imaging system.

First Embodiment

Figure 1:
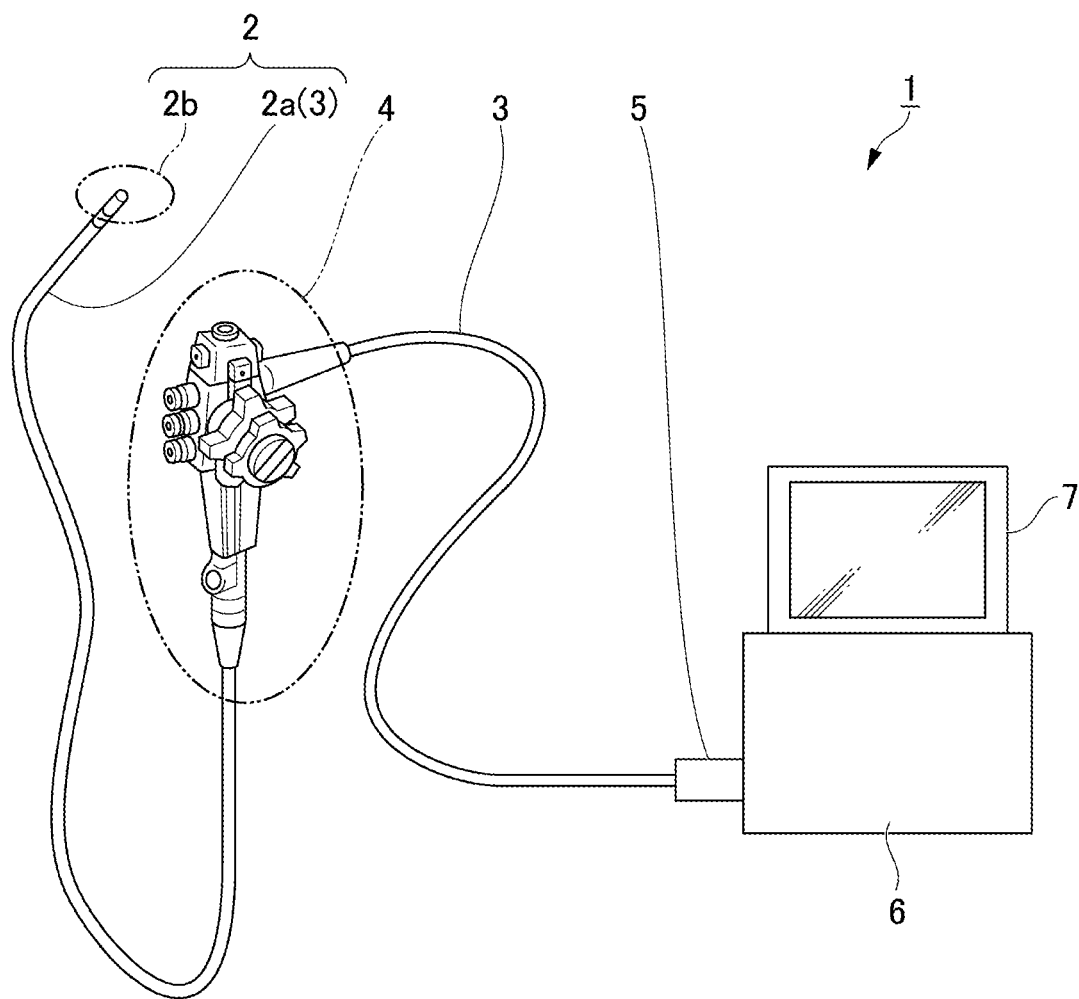
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a processor 6, and a display device 7. The endoscope insertion unit 2, the transmission cable 3, the operation unit 4, and the connector unit 5 constitute an endoscope.

Figure 2:
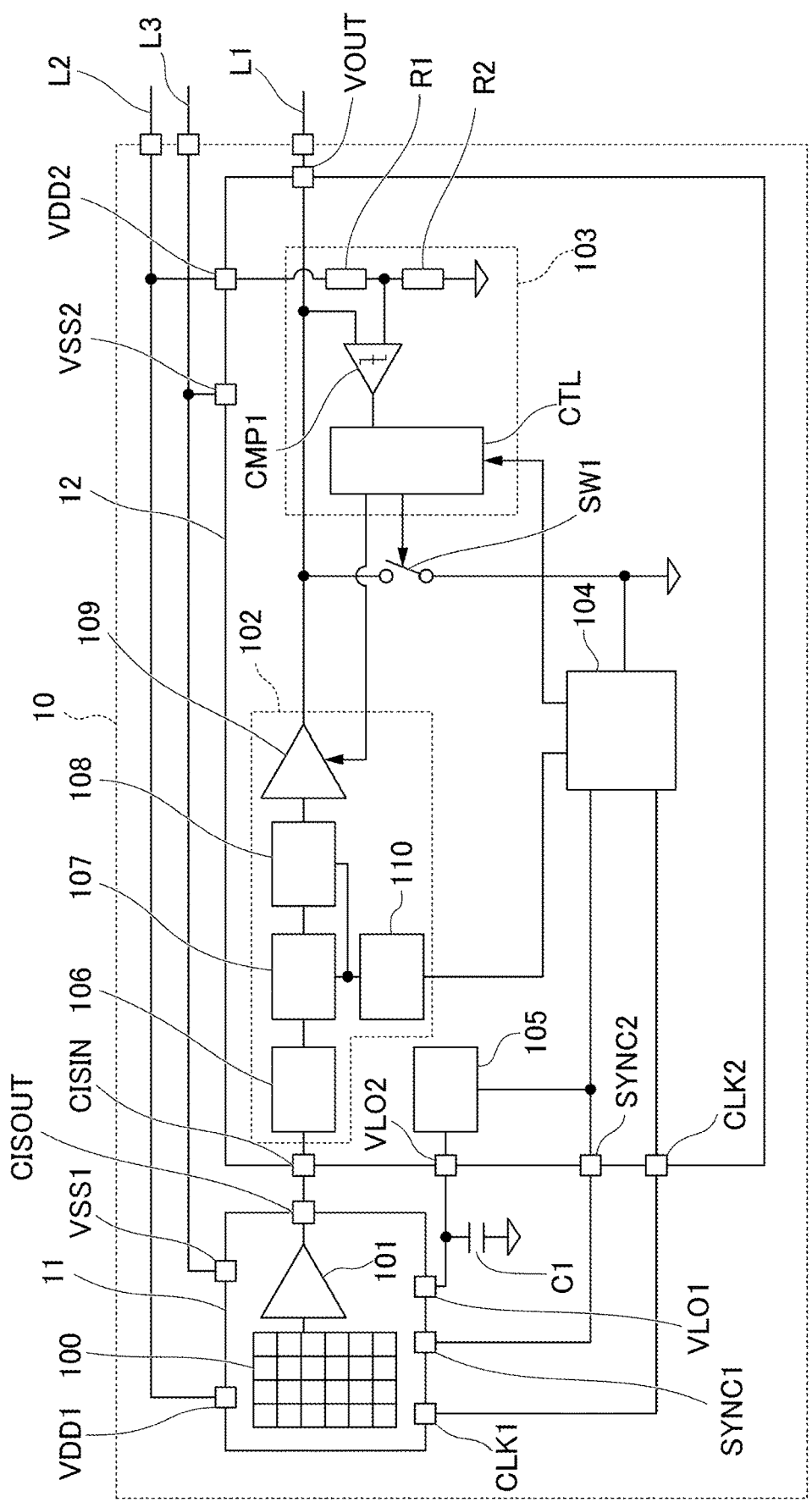
FIG. 2 is a block diagram showing a configuration of a camera unit included in the endoscope system according to a first embodiment of the present invention.

The endoscope insertion unit 2 includes an insertion unit 2a. The insertion unit 2a is part of the transmission cable 3. The insertion unit 2a is to be inserted into the inside of a subject. The endoscope insertion unit 2 generates video data by imaging the inside of the subject. The endoscope insertion unit 2 outputs the generated video data to the processor 6. A camera unit 10 shown in FIG. 2 is disposed in a distal end 2b of the insertion unit 2a. In the insertion unit 2a, the operation unit 4 is connected to the end part opposite to the distal end 2b. The operation unit 4 accepts various operations for the endoscope insertion unit 2 from a user.

The transmission cable 3 connects the camera unit 10 and the connector unit 5 together. The video data generated by the camera unit 10 are output to the connector unit 5 via the transmission cable 3.

The connector unit 5 is connected to the endoscope insertion unit 2 and the processor 6. The connector unit 5 performs predetermined processing on the video data output from the endoscope insertion unit 2. The connector unit 5 outputs the video data to the processor 6.

The processor 6 performs image-processing on the video data output from the connector unit 5. Furthermore, the processor 6 centrally controls the entire endoscope system 1.

The display device 7 displays a video on the basis of the video data processed by the processor 6. In addition, the display device 7 displays various kinds of information related to the endoscope system 1.

The endoscope system 1 includes a light source device that generates illumination light emitted to the subject. The light source device is not shown in FIG. 1.

Figure 3:
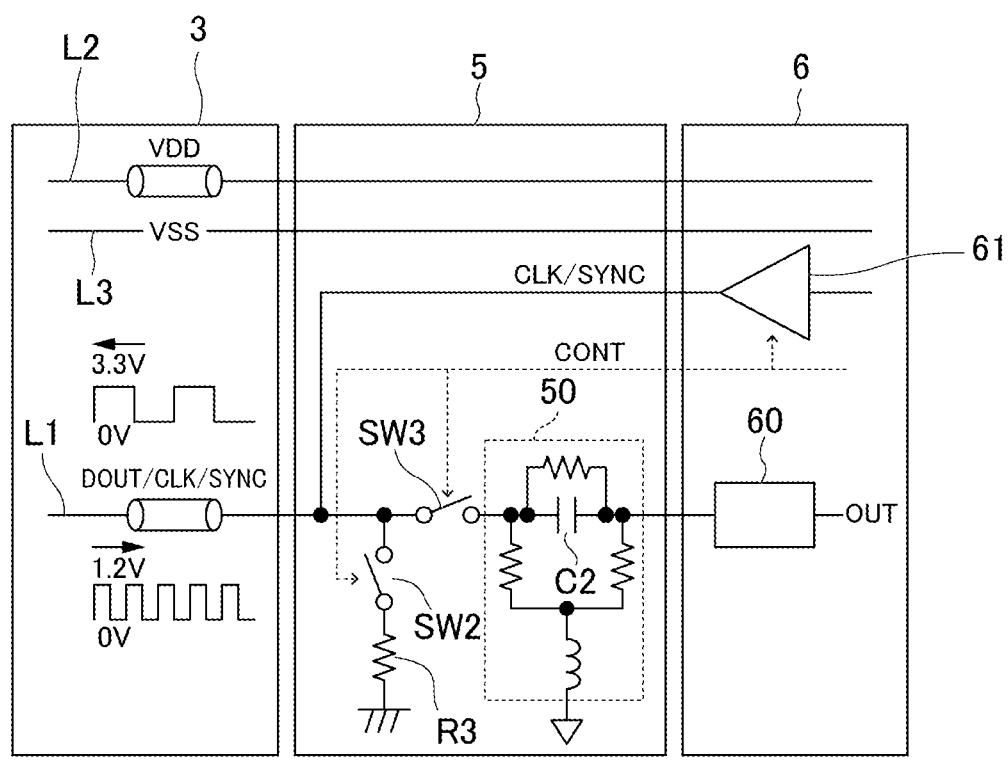
FIG. 3 is a block diagram showing a configuration of a connector unit and a processor included in the endoscope system according to a first embodiment of the present invention.

FIG. 2 and FIG. 3 show an internal configuration of the endoscope system 1. FIG. 2 shows a configuration of the camera unit 10. FIG. 3 shows a configuration of the connector unit 5 and the processor 6. In FIG. 2 and FIG. 3, the operation unit 4 and the display device 7 are not shown.

The processor 6 is a control unit. The camera unit 10 and the processor 6 are connected to each other by a signal line L1, a power source line L2, and a power source line L3. The signal line L1, the power source line 12, and the power source line L3 pass through the transmission cable 3.

A schematic configuration of the endoscope system 1 will be described. The processor 6 is connected to the camera unit 10 by the signal line L1 that transmits serial data and a system clock. The processor 6 operates on the basis of the system clock. The camera unit 10 includes an imager 11, a video output circuit 102, a clock-data-recovery (CDR) circuit 104 (camera-clock generation circuit), and a phase-locked loop (PLL) 110 (serial-clock generation circuit). The imager 11 generates an analog video signal on the basis of a camera clock. The video output circuit 102 converts the analog video signal into digital data and outputs serial data including the digital data to the signal line L1 on the basis of a serial clock having a higher frequency than the frequency of the camera clock. The CDR circuit 104 generates the camera clock synchronized with the system clock output to the signal line L1. The PLL 110 generates the serial clock synchronized with the system clock output to the signal line L1.

The processor 6 includes a video reception circuit 60 and a buffer 61 (system-clock output circuit). The video reception circuit 60 is electrically connected to the signal line L1 and receives the serial data. The buffer 61 outputs the system clock to the signal line L1 in a blanking period during which output of the serial data to the signal line L1 is stopped.

The communication mode of the endoscope system 1 is switched between a first mode and a second mode. The first mode is a communication mode for transmitting the serial data (video data) from the camera unit 10 to the processor 6. The second mode is a communication mode for transmitting the system clock of the processor 6 from the processor 6 to the camera unit 10. The imager 11 outputs the analog video signal in a video output period and stops output of the analog video signal in the blanking period. The communication mode of the endoscope system 1 is the first mode in the video output period and is the second mode in the blanking period.

A detailed configuration of the camera unit 10 will be described by referring to FIG. 2. The camera unit 10 includes the imager 11 and a control unit 12. The imager 11 is an imaging device (image sensor). The imager 11 includes a pixel unit 100 and a buffer 101.

The pixel unit 100 includes a plurality of pixels. The pixel unit 100 generates a pixel signal on the basis of light incident on the pixel unit 100. The imager 11 performs noise suppression, signal amplification, and the like on the pixel signal by using a circuit not shown in FIG. 2 and generates the analog video signal. The buffer 101 is used for enhancing the driving performance of the input analog video signal and outputting the analog video signal to the outside (control unit 12). When the communication mode is the first mode, the buffer 101 outputs the analog video signal to the control unit 12.

The imager 11 includes a pad VDD1, a pad VSS1, a pad CISOUT, a pad VLO1, a pad SYNC1, and a pad CLK1 in addition to the pixel unit 100 and the buffer 101. The pad VDD1 is connected to the power source line 12. The power source line L2 transmits a power source voltage from the processor 6 to the camera unit 10. The power source voltage is input to the pad VDD1. The pad VSS1 is connected to the power source line L3. The power source line 13 transmits a reference voltage lower than the power source voltage from the processor 6 to the camera unit 10. For example, the reference voltage is a ground voltage (0 V). The reference voltage is input to the pad VSS1.

A negative voltage for suppressing a dark current generated in the pixel unit 100 of the imager 11 is input to the pad VLO1. An imaging control signal for controlling reading of the pixel signal in the imager 11 is input to the pad SYNC1. The camera clock is input to the pad CLK1. The signal input to each pad of the imager 11 is supplied to the circuits in the imager 11. The imager 11 operates in synchronization with the camera clock.

The pad CISOUT is connected to the buffer 101. The analog video signal output front the buffer 101 is transmitted to the control unit 12 via the pad CISOUT.

The control unit 12 includes the video output circuit 102, a communication control circuit 103, the CDR circuit 104, a voltage generation circuit 105, and a switch SW1. A capacitance element C1 is connected to the imager 11 and the control unit 12.

The video output circuit 102 is electrically connected to the signal line L1 and outputs serial data generated on the basis of the analog video signal to the signal line L1. The video output circuit 102 includes an ADC 106, a serializer 107, an encoding circuit 108, a buffer 109, and the PLL 110.

The ADC 106 is an analog-to-digital conversion circuit. The ADC 106 is electrically connected to the imager 11. The analog video signal output from the imager 11 is input to the ADC 106. The ADC 106 converts the analog video signal into digital data (parallel data) including a plurality of parallel bits. The ADC 106 outputs the digital data to the serializer 107.

The serializer 107 converts the digital data into serial data. The serializer 107 outputs the serial data to the encoding circuit 108 at a timing synchronized with the serial clock. The encoding circuit 108 encodes the serial data output from the serializer 107. The encoding circuit 108 outputs the serial data to the buffer 109 at a timing synchronized with the serial clock, thus outputting the serial data to the signal line L1.

The camera unit 10 does not need to include the encoding circuit 108. In a case in which the camera unit 10 does not include the encoding circuit 108, the serializer 107 outputs the serial data to the buffer 109 at a timing synchronized with the serial clock, thus outputting the serial data to the signal line L1.

The PLL 110 generates the serial clock (transmission-side serial clock) on the basis of the camera clock. The electric potential of each of the system clock, the camera clock, and the serial clock is a high level or a low level. In each signal, the high level and the low level appear in turns. The timing at which the electric potential of each of the camera clock and the serial clock changes is synchronized with the timing at which the electric potential of the system clock changes. The frequency of the camera clock is the same as or different from that of the system clock. The frequency of the system clock is higher than that of the camera clock. For example, the frequency of the camera clock is 10 MHz. and the frequency of the system clock is higher than 100 MHz. The PLL 110 outputs the serial clock to the serializer 107 and the encoding circuit 108.

The buffer 109 is electrically connected to the signal line L1. The buffer 109 outputs the serial data output from the encoding circuit 108 to the signal line L1. The signal level of the serial data output to the signal line L1 is the high level or the low level. For example, the buffer 109 is a three-state buffer. The buffer 109 turns into any one of a high-level state, a low-level state, and a high-impedance state. The state of the buffer 109 switches between the high-level state, the low-level state, and the high-impedance state. The buffer 109 outputs the serial data to the signal line L1 by turning into the high-level state or the low-level state and turns into the high-impedance state in the blanking period. While the state of the buffer 109 is the high-impedance state, output of the serial data to the signal line L1 is stopped.

The buffer 109 operates at a lower voltage than the power source voltage. For example, the power source voltage is 3.3 V. When the state of the buffer 109 is the high-level state, the electric potential of the signal line L1 is, for example, 1.2 V. When the state of the buffer 109 is the low-level state, the electric potential of the signal line L1 is the same as the reference voltage.

Since the buffer 109 operates at a lower voltage than the power source voltage, the power consumption is reduced. In addition, a penetration current flowing in the buffer 109 is reduced. Due to the influence of the penetration current, the change of the power source voltage occurs in the transmission cable 3. The change of the power source voltage becomes small.

The switch SW1 includes a first terminal and a second terminal. The state of the switch SW1 becomes any one of an ON (short-circuit) state and an OFF (open) state. When the state of the switch SW1 is the ON state, the first terminal and the second terminal are electrically connected to each other. When the state of the switch SW1 is the OFF state, the first terminal and the second terminal are electrically insulated from each other.

The first terminal of the switch SW1 is electrically connected to the signal line L1, and the second terminal of the switch SW1 is connected to the CDR circuit 104. When the communication mode is the second mode, a control clock including the system clock and the imaging control signal is output from the processor 6 to the signal line L1. When the communication mode is the second mode, the state of the switch SW1 becomes the ON state. At this time, the control clock is output from the signal line L1 to the CDR circuit 104. The switch SW1 receives the control clock from the processor 6. When the communication mode is the first mode, the state of the switch SW1 becomes the OFF state.

The communication control circuit 103 includes a controller CTL, a comparator CMP1, a resistor R1, and a resistor R2. Each of the resistor R1 and the resistor R2 includes a first terminal and a second terminal. The first terminal of the resistor R1 is connected to the power source line L2. The power source voltage is input to the first terminal of the resistor R1. The first terminal of the resistor R2 is connected to the second terminal of the resistor R1. The reference voltage is input to the second terminal of the resistor R2. The resistor R1 and the resistor R2 generate a voltage on the basis of the power source voltage, the reference voltage, and the resistance value of each resistor.

The comparator CMP1 includes a first input terminal, a second input terminal, and an output terminal. The first input terminal of the comparator CMP1 is electrically connected to the signal line L1. The second input terminal of the comparator CMP1 is connected to the second terminal of the resistor R1 and the first terminal of the resistor R2. The output terminal of the comparator CMP1 is connected to the controller CTL.

The comparator CMP1 compares a voltage input to the first input terminal with a voltage input to the second input terminal. In other words, the comparator CMP1 compares the electric potential of the signal line L1 with a predetermined electric potential. For example, the predetermined electric potential is higher than the operation voltage (1.2 V) of the buffer 109 and is lower than the power source voltage (3.3 V). The comparator CMP1 outputs a signal indicating a comparison result to the controller CTL.

The controller CTL determines the electric potential of the signal line 11 on the basis of the signal output from the comparator CMP1. The controller CTL generates a control signal for controlling the state of each of the buffer 109 and the switch SW1 on the basis of the determined electric potential. The controller CTL outputs the generated control signal to each of the buffer 109 and the switch SW1. The controller CTL switches the communication modes between the first mode and the second mode.

The CDR circuit 104 is connected to the second terminal of the switch SW1. When the communication mode is the second mode, the control clock including the system clock and the imaging control signal is input to the CDR circuit 104 via the switch SW1. The CDR circuit 104 restores the system clock and the imaging control signal from the control clock. The CDR circuit 104 generates the camera clock on the basis of the system clock. The CDR circuit 104 outputs the camera clock to the imager 11 and the PLL 110. In addition, the CDR circuit 104 outputs the imaging control signal to the imager 11 and the voltage generation circuit 105.

The CDR circuit 104 includes a counter. The CDR circuit 104 starts execution of counting the camera clock at a timing at which the control clock is input from the signal line L1 to the CDR circuit 104 as a start point. When a predetermined number has been counted, the CDR circuit 104 outputs a control signal for switching the communication modes from the second mode to the first mode to the controller CTL. In addition, when the predetermined number has been counted, the CDR circuit 104 outputs the imaging control signal for causing the imager 11 to start output of the analog video signal to the imager 11.

The voltage generation circuit 105 generates a negative voltage in a horizontal blanking period indicated by the imaging control signal output from the CDR circuit 104 and outputs the negative voltage to the capacitance element C1. The capacitance element C1 holds the negative voltage and outputs the negative voltage to the imager 11.

The control unit 12 includes a pad VDD2, a pad VSS2, a pad CISIN, a pad VOUT, a pad VLO2, a pad SYNC2, and a pad CLK2 in addition to the video output circuit 102 and the like. The pad VDD2 is connected to the power source line L2. The power source voltage is input to the pad VDD2. The pad VSS2 is connected to the power source line L3. The reference voltage is input to the pad VSS2.

The pad CISIN is connected to the pad CISOUT and the ADC 106. The analog video signal is output from the pad CISOUT and is input to the pad CISIN. The analog video signal is output to the ADC 106 via the pad CISIN.

The pad VOUT is connected to the buffer 109, the first terminal of the switch SW1, and the first input terminal of the comparator CMP1. In addition, the pad VOUT is connected to the signal line L1. When the communication mode is the first mode, the serial data are output from the buffer 109 and are input to the pad VOUT. The serial data are output to the signal line L1 via the pad VOUT. When the communication mode is the second mode, the control clock is input from the signal line L1 to the pad VOUT. The control clock is output to the CDR circuit 104 via the pad VOUT and the switch SW1.

The pad VLO2 is connected to the voltage generation circuit 105 and the capacitance element C1. The negative voltage generated by the voltage generation circuit 105 in the horizontal blanking period is input to the pad VLO2. The negative voltage is output to the capacitance element C1 via the pad VLO2. The capacitance element C1 is connected to the pad VLO1 and the pad VLO2. The capacitance element C1 holds the negative voltage and outputs the negative voltage to the imager 11.

The pad SYNC2 is connected to the CDR circuit 104 and the pad SYNC1. The imaging control signal generated by the CDR circuit 104 is input to the pad SYNC1. The imaging control signal is output to the imager 11 via the pad SYNC2.

The pad CLK2 is connected to the CDR circuit 104 and the pad CLK1. The camera clock generated by the CDR circuit 104 is input to the pad CLK2 regardless of the communication mode. The camera clock is output to the imager 11 via the pad CLK2.

A switch may be disposed between the buffer 109 and the signal line L1. When the communication mode is the first mode, the state of the switch becomes the ON state. When the communication mode is the second mode, the state of the switch becomes the OFF state.

The camera unit 10 and the processor 6 are connected to each other by the signal line L1, the power source line L2, and the power source line L3. The power source line L2 transmits the power source voltage to be supplied to the imager 11 from the processor 6 to the camera unit 10. The power source line L3 transmits the reference voltage to be supplied to the imager 11 from the processor 6 to the camera unit 10. The reference voltage is lower than the power source voltage and is higher than the above-described negative voltage.

The transmission cable 3 includes a plurality of cables. For example, the transmission cable 3 includes a first cable and a second cable. The signal line LU is included in the first cable. The power source line L2 and the power source line 13 are included in the second cable. For example, the power source line L2 is disposed on the core side of the second cable, and the power source line L3 is disposed on the outer side of the second cable.

A detailed configuration of the connector unit 5 and the processor 6 will be described by referring to FIG. 3. The connector unit 5 includes an equalizer 50, a switch SW2, a switch SW3, and a resistor R3. The processor 6 includes the video reception circuit 60 and the buffer 61.

Each of the switch SW2 and the switch SW3 includes a first terminal and a second terminal. The state of each switch becomes any one of an ON state and an OFF state. When the state of each switch is the ON state, the first terminal and the second terminal are electrically connected to each other. When the state of each switch is the OFF state, the first terminal and the second terminal are electrically insulated from each other.

The first terminal of the switch SW2 is electrically connected to the signal line L1, and the second terminal of the switch SW2 is connected to the resistor R3. When the communication mode is the first mode, the state of the switch SW2 becomes the ON state. At this time, the resistor R3 for realizing impedance matching is electrically connected to the signal line L1. When the communication mode is the second mode, the state of the switch SW2 becomes the OFF state. At this time, the resistor R3 is electrically insulated from the signal line L1. The state of the switch SW2 is controlled on the basis of the control signal CONT.

The first terminal of the switch SW3 is electrically connected to the signal line L1, and the second terminal of the switch SW3 is connected to the equalizer 50. When the communication mode is the first mode, the state of the switch SW3 becomes the ON state. At this time, the equalizer 50 is electrically connected to the signal line L1, and the serial data (DOUT) are input to the equalizer 50. When the communication mode is the second mode, the state of the switch SW3 becomes the OFF state. At this time, the equalizer 50 is electrically insulated from the signal line L1. The state of the switch SW3 is controlled on the basis of the control signal CONT.

The equalizer 50 includes a capacitance element C2 and other elements. The equalizer 50 adjusts the frequency characteristics of the serial data. The equalizer 50 outputs the serial data of which the frequency characteristics are adjusted to the video reception circuit 60. The connector unit 5 does not need to include the equalizer 50.

The capacitance element C2 includes a first terminal and a second terminal. The first terminal of the capacitance element C2 is electrically connected to the signal line L1, and the second terminal of the capacitance element C2 is connected to the video reception circuit 60.

When continuous high level data constitute the serial data, the DC level of the second terminal of the capacitance element C2 increases. On the other hand, when continuous low level data constitute the serial data, the DC level of the second terminal of the capacitance element C2 decreases.

In order to restrict the above-described increase or decrease in the DC level, the encoding circuit 108 encodes the serial data. The serial data include two or more pieces of high level data and two or more pieces of low level data. The encoding circuit 108 encodes the serial data such that the sum of lengths of periods occupied by two or more pieces of high level data output to the signal line L1 is almost the same as the sum of lengths of periods occupied by two or more pieces of low level data output to the signal line L1.

For example, the encoding circuit 108 uses a Manchester code. When the serial data output from the serializer 107 are high level data, the encoding circuit 108 sequentially outputs the high level and the low level. One piece of data corresponding to the high level is converted into a combination of the high level and the low level. When the serial data output from the serializer 107 are low level data, the encoding circuit 108 sequentially outputs the low level and the high level. One piece of data corresponding to the low level is converted into a combination of the low level and the high level.

The length of a period during which the high level constituting a piece of data is output is the same as the length of a period during which the low level constituting a piece of data is output. For example, a case in which the serial data output from the serializer 107 include data of ten bits will be described. Regardless of whether each bit is the high level or the low level, the serial data are converted into a data string including ten pieces of high level data and ten pieces of low level data. The sum of lengths of periods occupied by the ten pieces of high level data is the same as the sum of lengths of periods occupied by the ten pieces of low level data.

When the communication mode is the first mode, the video reception circuit 60 receives the serial data. The video reception circuit 60 includes a decoding circuit that decodes the serial data encoded by the encoding circuit 108. In addition, the video reception circuit 60 includes a deserializer that converts the decoded serial data into parallel data including a plurality of parallel bits. The video reception circuit 60 generates the serial clock (reception-side serial clock) on the basis of the system clock and converts the serial data into the parallel data on the basis of the serial clock. The video reception circuit 60 outputs the parallel data (OUT) to a circuit not shown in FIG. 3. When the communication mode is the second mode, the state of the switch SW3 is the OFF state. Therefore, the video reception circuit 60 stops reception of the serial data. The processor 6 may transmit the serial clock (reception-side serial clock) generated in the video reception circuit 60 to the camera unit 10 via the signal line L1 in the blanking period as the system clock. In this case, the camera unit 10 generates a camera clock synchronized with the reception-side serial clock by using a PLL circuit or the like.

The video reception circuit 60 may be constituted by at least one of a processor circuit and a logic circuit. For example, the processor circuit is at least one of a central processing unit (CPU), a digital signal processor (DSP), and a graphics-processing unit (GPU). For example, the logic circuit is at least one of an application-specific integrated circuit (ASIC) and a field-programmable gate array (FPGA). The video reception circuit 60 may include one or a plurality of processor circuits. The video reception circuit 60 may include one or a plurality of logic circuits.

The video reception circuit 60 may read a program and execute the read program. The program includes commands defining the operations of the video reception circuit 60. In other words, the functions of the video reception circuit 60 may be realized by software. The program, for example, may be provided by using a "computer-readable recording medium" such as a flash memory. The program may be transmitted from the computer storing the program to the processor 6 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

The buffer 61 is electrically connected to the signal line L1. A control clock generated by a signal generation circuit not shown in FIG. 3 is input to the buffer 61. The control clock includes the system clock and the imaging control signal.

When the communication mode is the second mode, the buffer 61 outputs the control clock (CLK/SYNC) to the signal line L1. For example, the buffer 61 is a three-state buffer. The buffer 61 turns into any one of a high-level state, a low-level state, and a high-impedance state. The state of the buffer 61 switches between the high-level state, the low-level state, and the high-impedance state. When the communication mode is the second mode, the buffer 61 outputs the control clock to the signal line L1 by turning into the high-level state or the low-level state.

When the communication mode is the first mode, the buffer 61 turns into the high-impedance state. While the state of the buffer 61 is the high-impedance state, output of the control clock to the signal line L1 is stopped. The state of the buffer 61 is controlled on the basis of the control signal CONT.

The video reception circuit 60 and the buffer 61 operate on the basis of the system clock of the processor 6. All or part of the video reception circuit 60 and the buffer 61 may be disposed in the operation unit 4 or the connector unit 5.

A switch may be disposed between the signal line L1 and the buffer 61. When the communication mode is the second mode, the state of the switch becomes the ON state. When the communication mode is the first mode, the state of the switch becomes the OFF state.

The imaging control signal does not need to be transmitted from the processor 6 to the camera unit 10. In the camera unit 10, the imaging control signal may be generated on the basis of the camera clock.

Figure 4:
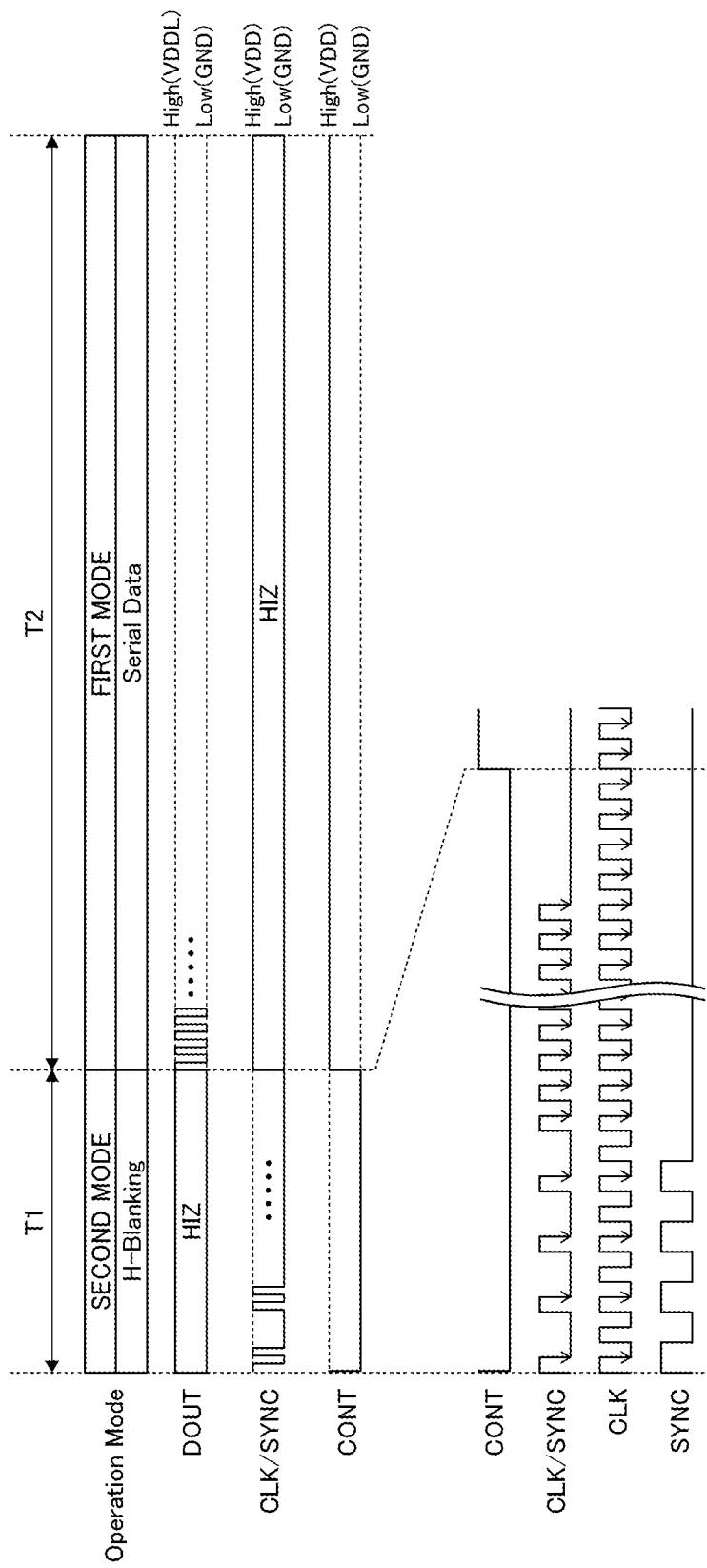
FIG. 4 is a timing chart of communication in the endoscope system according to a first embodiment of the present invention.

FIG. 4 shows timings of communication in the endoscope system 1. Time passes in the right direction in FIG. 4. In FIG. 4, the operation mode of the imager 11, the serial data (DOUT), the control clock (CLK/SYNC), and the control signal CONT are shown.

In FIG. 4, the operation in a horizontal blanking period T1 and a video output period T2 is shown. The control signal CONT and the control clock (CLK/SYNC) in the horizontal blanking period T1 are shown. In addition, the camera clock CLK and the imaging control signal SYNC restored by the CDR circuit 104 in the horizontal blanking period T1 are shown.

In the horizontal blanking period T1, the communication mode is the second mode. In the horizontal blanking period T1, the state of the buffer 109 is the high-impedance state, and the state of the switch SW1 is the ON state. In the horizontal blanking period T1, the state of the switch SW2 and the switch SW3 is the OFF state. In the horizontal blanking period T1, the electric potential of the control signal CONT is at the low level.

When the communication modes are switched from the second mode to the first mode, the video output period T2 is started. An operation in the video output period T2 will be described. In the video output period T2, the communication mode is the first mode. When the video output period T2 is started, the controller CTL disables the high-impedance state of the buffer 109 and sets the state of the switch SW1 to the OFF state. In the video output period T2, the imager 11 outputs the analog video signal. The serial data generated by the serializer 107 are output to the signal line L1 via the encoding circuit 108 and the buffer 109.

When the video output period T2 is started, the electric potential of the control signal CONT is set at the high level. At this time, the state of the buffer 61 becomes the high-impedance state, and the state of the switch SW2 and the switch SW3 becomes the ON state. The buffer 61 stops output of the control clock. Since the state of the switch SW3 becomes the ON state, the serial data output to the signal line L1 are input to the video reception circuit 60. The video reception circuit 60 receives the serial data.

The high level of the serial data output to the signal line L1 is VDDL. This high level VDDL is lower than the power source voltage VDD. Therefore, the controller CTL determines that the serial data are output to the signal line L1. The controller CTL maintains the state of the switch SW1 in the OFF state in order to transmit the serial data.

The imager 11 stops output of the analog video signal in the blanking period. A plurality of blanking periods of the imager 11 include a vertical blanking period and a horizontal blanking period. The vertical blanking period is disposed between a timing at which reading of the video data of one frame is completed and a timing at which reading of the video data of next one frame is started. The horizontal blanking period is disposed between a timing at which reading of the video data of one row in one frame is completed and a timing at which reading of the video data of next one row in the same frame is started. The video data of one frame include video data of multiple rows. An operation in the vertical blanking period will not be described.

An operation in the horizontal blanking period T1 will be described. When the horizontal blanking period T1 is started, the electric potential of the control signal CONT is set at the low level. At this time, the high-impedance state of the buffer 61 is disabled, and the state of the switch SW2 and the switch SW3 becomes the OFF state. The buffer 61 starts output of the control clock. Since the state of the switch SW3 becomes the OFF state, the video reception circuit 60 is electrically insulated from the signal line L1 and stops reception of the serial data.

The signal level of the control clock output to the signal line L1 is the high level or the low level. The high level of the control clock is the same as the power source voltage VDD and is higher than the high level VDDL of the serial data. When the control clock having the high level is output to the signal line L1, the controller CTL determines that the control clock is output to the signal line L1. The controller CTL sets the state of the buffer 109 to the high-impedance state and sets the state of the switch SW1 to the ON state. At this time, the communication modes are switched from the first mode to the second mode.

The buffer 109 stops output of the serial data. Since the state of the switch SW1 becomes the ON state, the control clock transmitted by the signal line L1 is input to the CDR circuit 104. The CDR circuit 104 restores the system clock and the imaging control signal from the control clock. The CDR circuit 104 generates the camera clock on the basis of the system clock. For example, the camera clock is synchronized with the falling edge of the system clock.

The CDR circuit 104 outputs the camera clock to the imager 11 and the PILL 110. In addition, the CDR circuit 104 outputs the imaging control signal to the imager 11 and the voltage generation circuit 105. The voltage generation circuit 105 generates the negative voltage and outputs the negative voltage to the capacitance element C1. The capacitance element C1 holds the negative voltage and outputs the negative voltage to the imager 11.

In a 4-transistor-type CMOS imager, a dark current can be reduced by applying a negative electric potential to a transfer gate (TG) in a signal accumulation period. The negative voltage VLO is supplied to the transfer gate in the imager 11.

When the communication modes are switched from the first mode to the second mode, the CDR circuit 104 starts execution of counting on the basis of the control clock. When a predetermined clock number is counted, the CDR circuit 104 outputs the imaging control signal for starting reading of a pixel signal in the imager 11 to the imager 11. At this time, the CDR circuit 104 outputs a control signal for switching the communication modes to the controller CTL. The controller CTL disables the high-impedance state of the buffer 109 and sets the state of the switch SW1 to the OFF state on the basis of the control signal output from the CDR circuit 104. At this time, the communication modes are switched from the second mode to the first mode, and the video output period T2 is started. In the video output period T2, the operation described above is executed.

In the above description, the CDR circuit 104 outputs the control signal for switching the communication modes from the second mode to the first mode to the controller CTL. At a timing at which the communication modes are switched from the second mode to the first mode, the CDR circuit 104 may output a control signal for controlling the state of the buffer 109 to the buffer 109 and may output a control signal for controlling the state of the switch SW1 to the switch SW1.

A method of switching the communication modes of the endoscope system 1 is not limited to the above-described method. As long as the serial data are output to the signal line L1 in the video output period and the control clock is output to the signal line L1 in the blanking period, any method may be used for switching the communication modes of the endoscope system 1.

In the first embodiment, the system clock of the processor 6 and the serial data are transmitted by one signal line L1. Therefore, the number of signal lines is reduced. The PLL 110 generates the serial clock on the basis of the camera clock. The serial data are output to the signal line L1 at a timing synchronized with the serial clock. Therefore, the endoscope system 1 can transmit high-speed serial data.

In a system in which an analog video signal is transmitted by using a thin and long cable, the amplitude of a video signal is significantly attenuated, and the quality of an image deteriorates. In the endoscope system 1, the analog video signal is converted into the digital data, and the digital data are transmitted by the transmission cable 3. Therefore, deterioration of the quality of an image is restricted. In addition, the resistance to jitter is improved.

First Modified Example of First Embodiment

Figure 5:
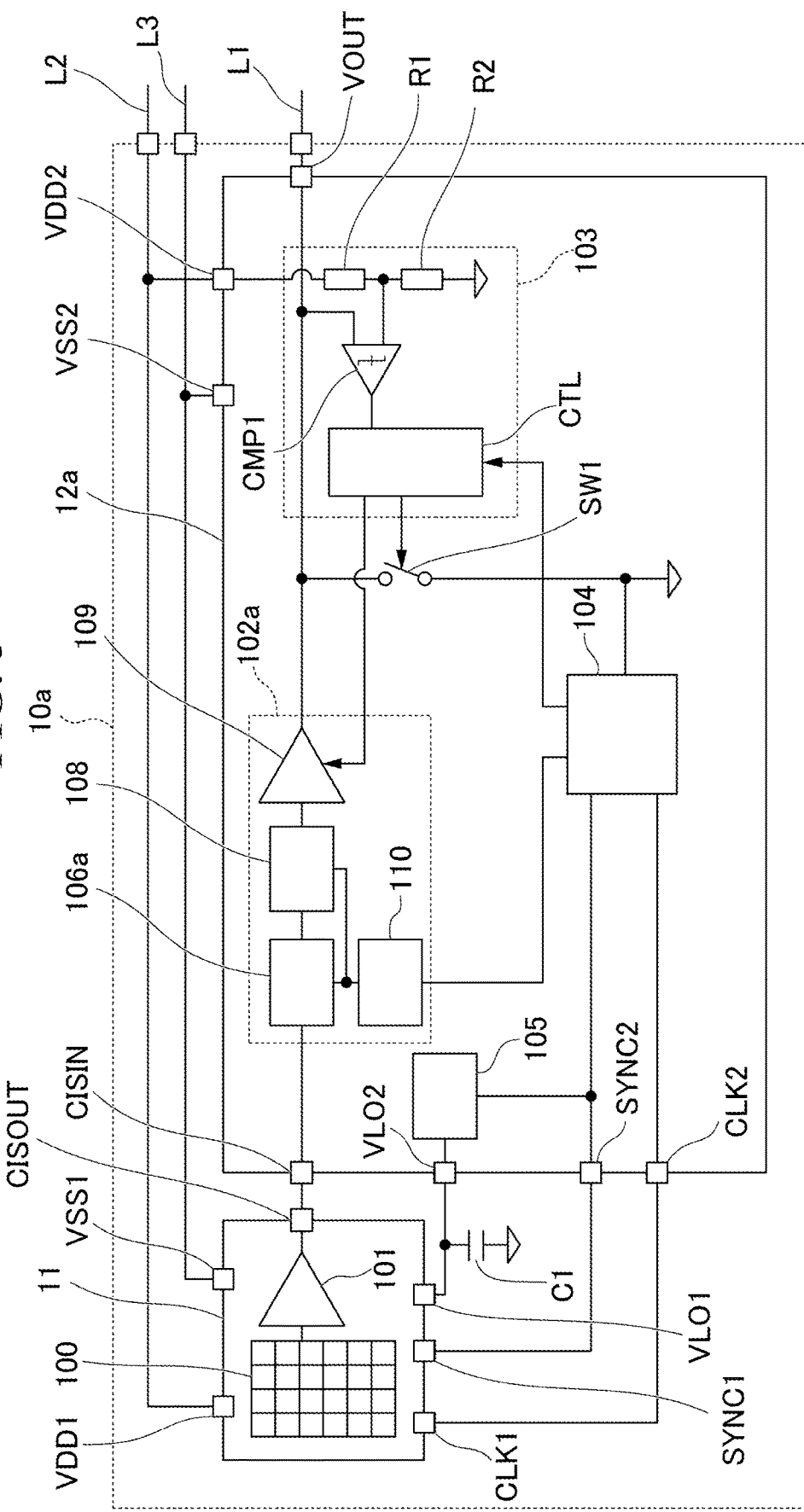
FIG. 5 is a block diagram showing a configuration of a camera unit included in an endoscope system according to a first modified example of the first embodiment of the present invention.

In a first modified example of the first embodiment of the present invention, the camera unit 10 shown in FIG. 2 is changed to a camera unit 10a shown in FIG. 5. FIG. 5 shows a configuration of the camera unit 10a. The same configuration as that shown in FIG. 2 will not be described.

The control unit 12 shown in FIG. 2 is changed to a control unit 12a. In the control unit 12a, the video output circuit 102 shown in FIG. 2 is changed to a video output circuit 102a. In the video output circuit 102a, the ADC 106 shown in FIG. 2 is changed to an ADC 106a. The video output circuit 102a does not include the serializer 107 shown in FIG. 2.

The PLL 110 generates a serial clock and outputs the serial clock to the ADC 106a and the encoding circuit 108. The analog video signal output from the imager 11 is input to the ADC 106a. The ADC 106a has a function of a serializer in addition to a function of AD conversion. The ADC 106a converts the analog video signal into serial data and outputs the serial data to the encoding circuit 108 at a timing synchronized with the serial clock. In a case in which the camera unit 10a does not include the encoding circuit 108, the ADC 106a outputs the serial data to the buffer 109 at a timing synchronized with the serial clock, thus outputting the serial data to the signal line L1.

In the first modified example of the first embodiment, a serializer independent of the ADC 106a is unnecessary.

Second Modified Example of First Embodiment

Figure 6:
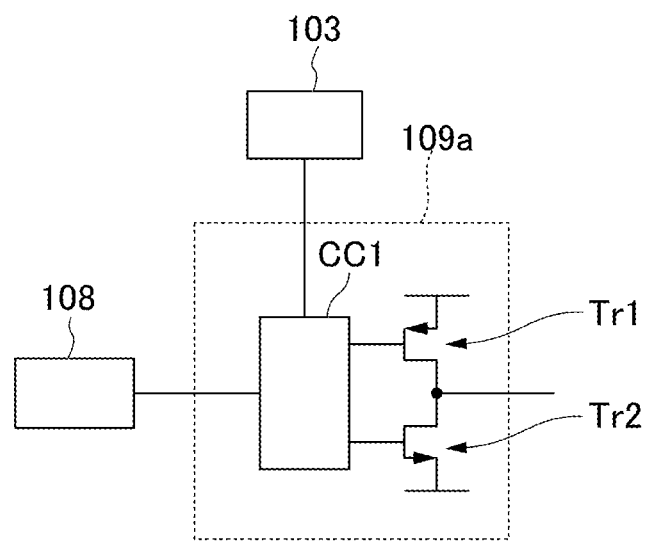
FIG. 6 is a circuit diagram showing a configuration of a buffer included in an endoscope system according to a second modified example of the first embodiment of the present invention.

In a second modified example of the first embodiment of the present invention, the buffer 109 shown in FIG. 2 is changed to a buffer 109a shown in FIG. 6. FIG. 6 shows a configuration of the buffer 109a.

The buffer 109a includes a control circuit CC1, a transistor Tr1, and a transistor Tr2. The serial data output from the encoding circuit 108 are input to the control circuit CC1. In addition, a mode signal indicating the communication mode of the endoscope system 1 is output from the communication control circuit 103 and is input to the control circuit CC1. The control circuit CC1 generates a signal for controlling each of the transistor Tr1 and the transistor Tr2 on the basis of the signal level of each of the serial data and the mode signal.

The transistor Tr1 is a PMOS transistor, and the transistor Tr2 is an NMOS transistor. Each of the transistor Tr and the transistor Tr2 includes a gate, a source, and a drain.

The power source voltage is input to the source of the transistor Tr1. The signal output from the control circuit CC) is input to the gate of the transistor Tr1. The drain of the transistor Tr1 and the drain of the transistor Tr2 are connected to each other. The drain of each of the transistor Tr1 and the transistor Tr2 is electrically connected to the signal line L1. The signal output from the control circuit CC1 is input to the gate of the transistor Tr2. The reference voltage is input to the source of the transistor Tr2.

When the mode signal indicates the first mode, the control circuit CC1 outputs a signal having the high level or the low level to the transistor Tr1 and the transistor Tr2. The electric potential of the signal input to the gate of the transistor Tr1 is the same as the electric potential of the signal input to the gate of the transistor Tr2. When the signal having the high level is output to the transistor Tr1 and the transistor Tr2, the state of the transistor Tr1 becomes the OFF state and the state of the transistor Tr2 becomes the ON state. Therefore, the buffer 109a outputs a signal having the low level to the signal line L1. When the signal having the low level is output to the transistor Tr and the transistor Tr2, the state of the transistor Tr1 becomes the ON state and the state of the transistor Tr2 becomes the OFF state. Therefore, the buffer 109a outputs a signal having the high level to the signal line L1.

When the mode signal indicates the second mode, the control circuit CC1 outputs a signal having the high level to the transistor Tr1 and outputs a signal having the low level to the transistor Tr2. At this time, the state of each of the transistor Tr1 and the transistor Tr2 becomes the OFF state. Therefore, the state of the buffer 109a becomes the high-impedance state.

The ADC 106 and the serializer 107 may be changed to the ADC 106a shown in FIG. 5.

In the second modified example of the first embodiment, when the communication mode of the endoscope system 1 is the first mode, only one of the transistor Tr1 and the transistor Tr2 becomes the ON state. Therefore, a penetration current flowing from the source of the transistor Tr1 to the source of the transistor Tr2 is significantly reduced, and the change of the power source voltage in the transmission cable 3 becomes small.

Second Embodiment

Figure 7:
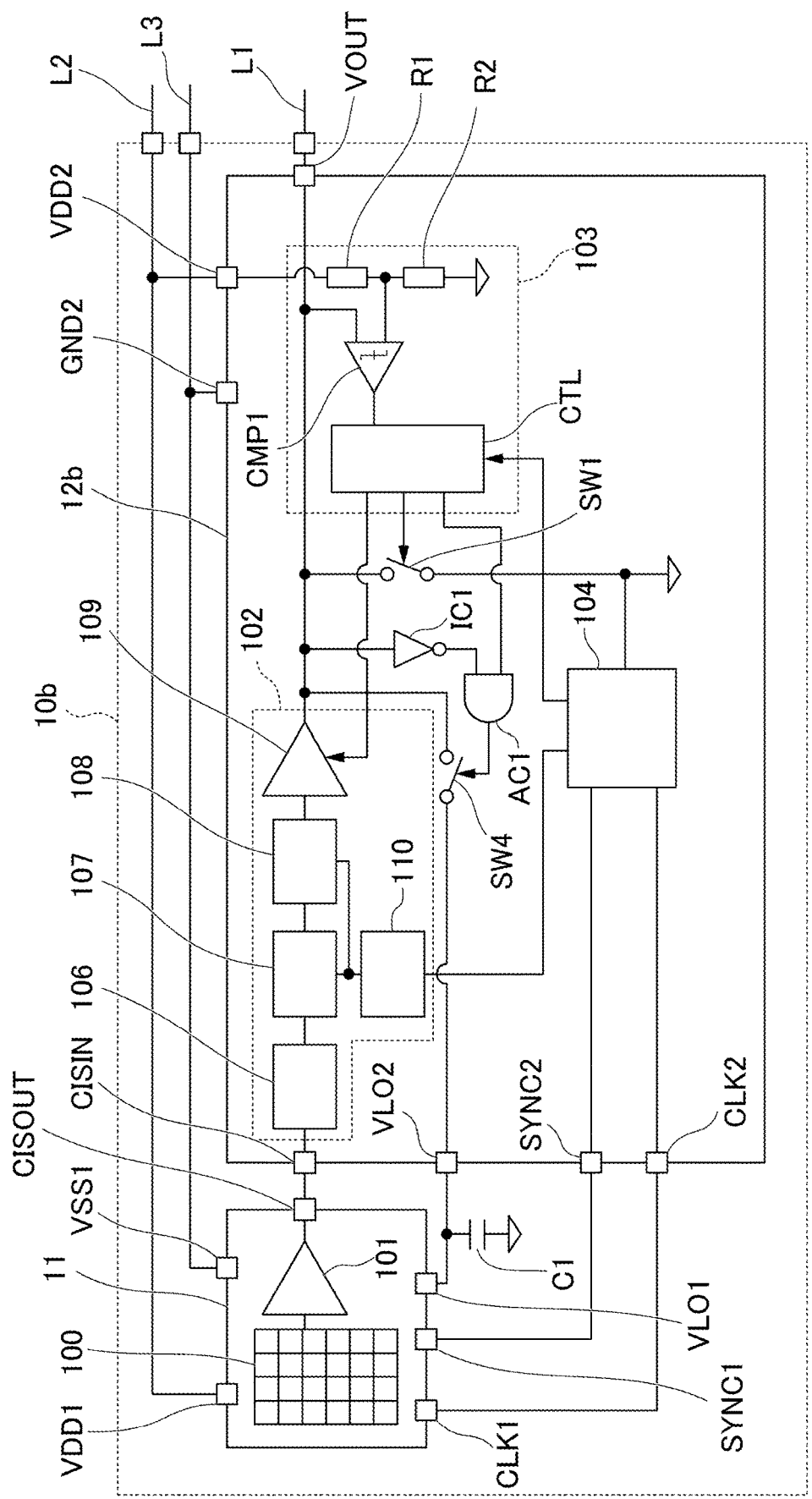
FIG. 7 is a block diagram showing a configuration of a camera unit included in an endoscope system according to a second embodiment of the present invention.

In a second embodiment of the present invention, the camera unit 10 shown in FIG. 2 is changed to a camera unit 10b shown in FIG. 7. FIG. 7 shows a configuration of the camera unit 10b. The same configuration as that shown in FIG. 2 will not be described.

The control unit 12 shown in FIG. 2 is changed to a control unit 12b. The control unit 12b includes a video output circuit 102, a communication control circuit 103, a CDR circuit 104, a switch SW1, a switch SW4, an inverter IC1, and an AND circuit AC1 (control circuit). The control unit 12b does not include the voltage generation circuit 105 shown in FIG. 2.

When the communication mode is the second mode, the control clock including the system clock and the imaging control signal is output from the processor 6 to the signal line L1. The signal level of the control clock is the high level or the low level. The high level of the control clock is higher than the high level VDDL of the serial data and is lower than the power source voltage. For example, the high level VDDL of the serial data is 1.2 V, the power source voltage is 3.3 V, and the high level of the control clock is 2.3 V. The low level of the control clock is a negative voltage. For example, the negative voltage is −1.0 V.

The buffer 61 outputs the control clock alternately including a positive voltage (high level) and a negative voltage (low level) to the signal line L1. In a case in which only the system clock is transmitted to the camera unit 10b and the imaging control signal is not transmitted to the camera unit 10b, the buffer 61 outputs the system clock alternately including a positive voltage and a negative voltage to the signal line L1.

The switch SW4 includes a first terminal and a second terminal. The state of the switch SW4 becomes any one of an ON state and an OFF state. When the state of the switch SW4 is the ON state, the first terminal and the second terminal are electrically connected to each other. When the state of the switch SW4 is the OFF state, the first terminal and the second terminal are electrically insulated from each other.

The first terminal of the switch SW4 is electrically connected to the signal line L1, and the second terminal of the switch SW4 is electrically connected to the capacitance element C1. When the communication mode is the second mode and the negative voltage is output to the signal line L1, the state of the switch SW4 becomes the ON state. At this time, the capacitance element C1 is electrically connected to the signal line L1, and a negative voltage is output from the signal line L1 to the capacitance element C1. When the communication mode is the second mode and a positive voltage is output to the signal line L1, the state of the switch SW4 becomes the OFF state. At this time, the capacitance element C1 is electrically insulated from the signal line L1. When the communication mode is the first mode, the state of the switch SW4 becomes the OFF state. The state of the switch SW4 is controlled on the basis of the signal output from the AND circuit AC1.

The inverter IC1 includes a first terminal and a second terminal. The first terminal of the inverter IC1 is electrically connected to the signal line L1, and the second terminal of the inverter IC1 is connected to the AND circuit AC1. The inverter C1 outputs a signal having an electric potential acquired by inverting the electric potential of the signal line L1 to the AND circuit ACL. When the electric potential of the signal line L1 is at the high level, the inverter IC1 outputs a signal having the low level to the AND circuit AC1. When the electric potential of the signal line L1 is at the low level, the inverter IC1 outputs a signal having the high level to the AND circuit AC1.

The controller CTL of the communication control circuit 103 outputs a signal having the high level or the low level to the AND circuit AC1. The signal output from the inverter IC1 and the signal output front the controller CTL are input to the AND circuit AC1. The AND circuit AC1 outputs a signal indicating a result of an AND operation of the two input signals to the switch SW4.

When the communication mode is the second mode, the controller CTL outputs a signal having the high level to the AND circuit AC1. When the control clock having the low level (negative voltage) is output to the signal line L1, the inverter IC1 outputs a signal having the high level to the AND circuit AC1. At this time, the AND circuit AC1 outputs a signal having the high level to the switch SW4. The state of the switch SW4 becomes the ON state. Therefore, the negative voltage output to the signal line L1 is input to the capacitance element C1. When the control clock having the high level (positive voltage) is output to the signal line L1, the inverter IC1 outputs a signal having the low level to the AND circuit AC1. At this time, the AND circuit AC1 outputs a signal having the low level to the switch SW4. The state of the switch SW4 becomes the OFF state. Therefore, when the negative voltage is output to the signal line L1, the AND circuit AC1 sets the state of the switch SW4 to the ON state. When the positive voltage is output to the signal line L1, the AND circuit AC1 sets the state of the switch SW4 to the OFF state.

When the communication mode is the first mode, the controller CTL outputs a signal having the low level to the AND circuit AC1. At this time, the AND circuit AC1 outputs a signal having the low level to the switch SW4. The state of the switch SW4 becomes the OFF state.

The voltage output from the buffer 61 to the signal line L1 is attenuated while the voltage passes through the signal line L1. In a case in which a negative voltage necessary in the imager 11 is −1.0 V, the buffer 61 needs to output a lower voltage than −1.0 V to the signal line L1. The buffer 61 may output a system clock including a lower negative voltage than a design voltage (−1.0 V) designed for the imager 11 to the signal line L1 such that the negative voltage input to the capacitance element C1 almost matches the design voltage. The design voltage is necessary for the operation of the imager 11 and is defined in accordance with the specifications of the imager 11.

The ADC 106 and the serializer 107 may be changed to the ADC 106a shown in FIG. 5. The buffer 109 may be changed to the buffer 109a shown in FIG. 6.

In the second embodiment, since the negative voltage is supplied from the processor 6 to the imager 11, the camera unit 10b does not need to include the voltage generation circuit 105. Therefore, the camera unit 10b can be miniaturized.

Third Embodiment

Figure 8:
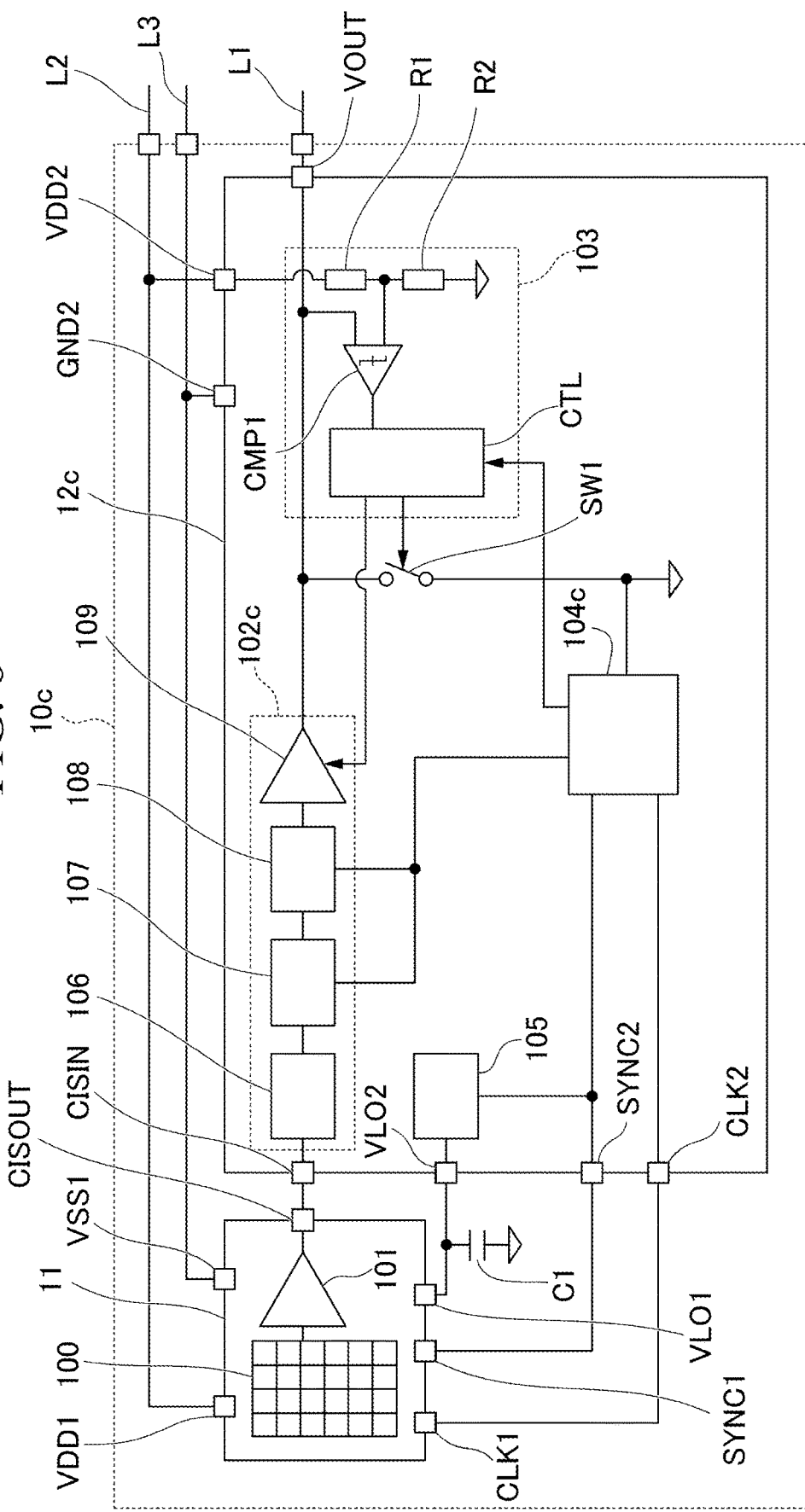
FIG. 8 is a block diagram showing a configuration of a camera unit included in an endoscope system according to a third embodiment of the present invention.

In a third embodiment of the present invention, the camera unit 10 shown in FIG. 2 is changed to a camera unit 10c shown in FIG. 8. FIG. 8 shows a configuration of the camera unit 10c. The same configuration as that shown in FIG. 2 will not be described.

The control unit 12 shown in FIG. 2 is changed to a control unit 12c. In the control unit 12c, the video output circuit 102 shown in FIG. 2 is changed to a video output circuit 102c. The video output circuit 102c does not include the PLL 110 shown in FIG. 2. In the control unit 12c, the CDR circuit 104 shown in FIG. 2 is changed to a CDR circuit 104c.

Figure 9:
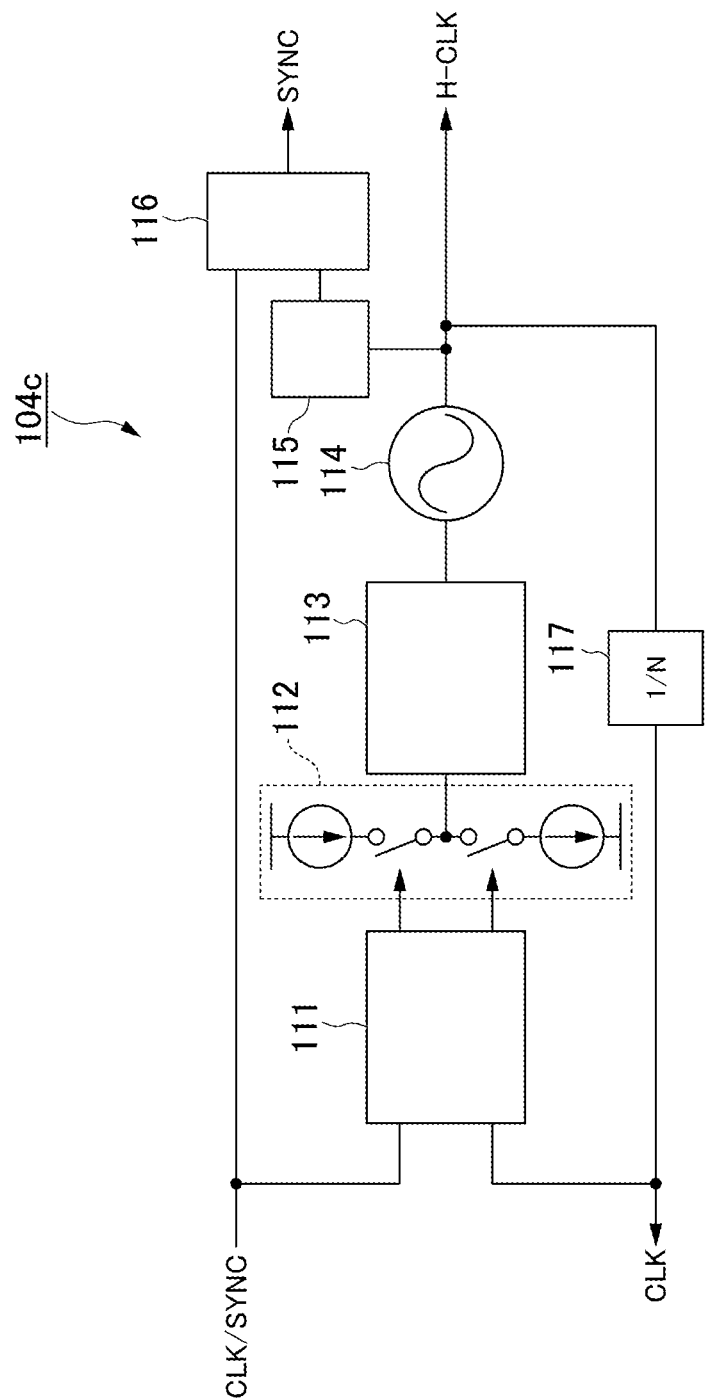
FIG. 9 is a block diagram showing a configuration of a CDR circuit included in the endoscope system according to the third embodiment of the present invention.

FIG. 9 shows a configuration of the CDR circuit 104c. The CDR circuit 104c shown in FIG. 9 includes a phase comparison circuit 111, a charge pump 112, a loop filter 113, an oscillator 114 (serial-clock generation circuit), a delay circuit 115, a logic circuit 16, and a frequency divider 117 (camera-clock generation circuit).

The control clock (CLK/SYNC) output from the signal line L1 and the camera clock (CLK) output from the frequency divider 117 are input to the phase comparison circuit 111. The phase comparison circuit 111 outputs a signal in accordance with the shift of the phase and frequency between the control clock and the camera clock to the charge pump 112. The charge pump 112 generates, on the basis of the signal output from the phase comparison circuit 111, an analog signal used for adjusting the frequency of the camera clock. The loop filter 113 outputs a control voltage to the oscillator 114 on the basis of the analog signal output from the charge pump 112.

The oscillator 114 is a voltage-controlled oscillator (VCO). The oscillator 114 generates a serial clock (H-CLK) having a frequency corresponding to the control voltage output from the loop filter 113. The oscillator 114 outputs the serial clock (transmission-side serial clock) to the serializer 107, the encoding circuit 108, and the frequency divider 117. The frequency divider 117 divides the frequency of the serial clock output from the oscillator 114, thus generating the camera clock. The frequency divider 117 converts the frequency of the serial clock to a lower frequency, thus generating the camera clock. The frequency divider 117 outputs the camera clock to the phase comparison circuit 111 and the imager 11.

When the communication mode is the first mode, the phase comparison circuit 111 stops comparison of the phase and the frequency between the control clock and the camera clock. Therefore, the frequency of the camera clock output from the frequency divider 117 does not change.

The delay circuit 115 delays the serial clock output from the oscillator 114. The delay circuit 115 outputs the delayed serial clock to the logic circuit 116.

The logic circuit 116 is a D flip-flop. The logic circuit 116 captures the control clock at a timing indicated by a rising edge of the delayed serial clock and outputs the imaging control signal (SYNC) to the imager 11 and the voltage generation circuit 105. For example, when the control clock is in the high level, the logic circuit 116 outputs the high level. When the control clock is in the low level, the logic circuit 116 outputs the low level.

The ADC 106 and the serializer 107 may be changed to the ADC 106a shown in FIG. 5. The buffer 109 may be changed to the buffer 109a shown in FIG. 6. The control unit 12b does not need to include the voltage generation circuit 105 and may include the switch SW4, the inverter IC1, and the AND circuit AC1 shown in FIG. 7.

In the third embodiment, the CDR circuit 104c can generate the serial clock by using a simple configuration. The camera unit 10c does not need to include the PLL 110. Therefore, the camera unit 10c can be miniaturized. It is possible to generate a highly accurate clock by using frequency division compared to frequency multiplication. Therefore, it is effective to generate a serial clock on the basis of a system clock and generate a camera clock by dividing the frequency of the serial clock. As with the first embodiment, the video reception circuit 60 generates the serial clock (reception-side serial clock) on the basis of the system clock and converts the serial data into parallel data on the basis of the serial clock. The processor 6 may transmit the serial clock (reception-side serial clock) generated in the video reception circuit 60 to the camera unit 10c via the signal line L1 as a system clock in the blanking period. In this case, the camera unit 10c generates a serial clock (transmission-side serial clock) synchronized with the reception-side serial clock by using a PLL circuit or the like.

Fourth Embodiment

Figure 10:
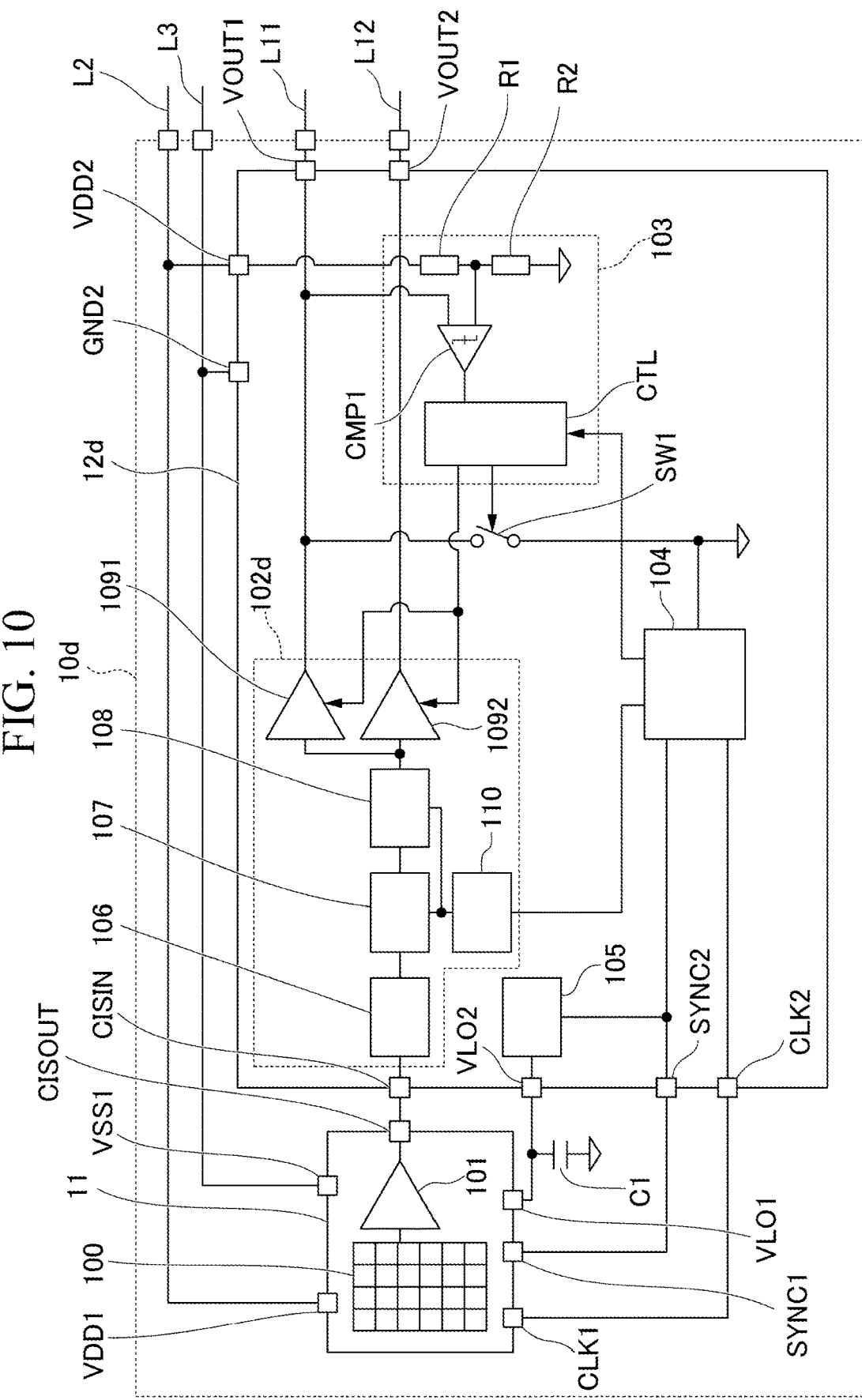
FIG. 10 is a block diagram showing a configuration of a camera unit included in an endoscope system according to a fourth embodiment of the present invention.

In a fourth embodiment of the present invention, the camera unit 10 shown in FIG. 2 is changed to a camera unit 10d shown in FIG. 10. FIG. 10 shows a configuration of the camera unit 10d. The same configuration as that shown in FIG. 2 will not be described.

The control unit 12 shown in FIG. 2 is changed to a control unit 12d. In the control unit 12d, the video output circuit 102 shown in FIG. 2 is changed to a video output circuit 102d. In the video output circuit 102d, the buffer 109 shown in FIG. 2 is changed to a buffer 1091 and a buffer 1092.

The encoding circuit 108 outputs serial data as a differential signal. The differential signal includes a first signal and a second signal having opposite phases to each other. The phase difference between the first signal and the second signal is 180 degrees. The encoding circuit 108 outputs the first signal to the buffer 1091 and outputs the second signal to the buffer 1092. The buffer 1091 is electrically connected to a signal line L11, and the buffer 1092 is electrically connected to a signal line L12. The buffer 1091 outputs the first signal output from the encoding circuit 108 to the signal line L11. The buffer 1092 outputs the second signal output from the encoding circuit 108 to the signal line L12. The level of the first signal output to the signal line L11 and the second signal output to the signal line L12 is the high level or the low level. When the level of the first signal is the high level, the level of the second signal is the low level. When the level of the first signal is the low level, the level of the second signal is the high level. For example, each of the buffer 1091 and the buffer 1092 is a three-state buffer as with the buffer 109 in the first embodiment.

The pad VOUT shown in FIG. 2 is changed to a pad VOUT1 and a pad VOUT2. The pad VOUT1 is connected to the buffer 1091, the first terminal of the switch SW1, the first input terminal of the comparator CMP1, and the signal line L11. The pad VOUT2 is connected to the buffer 1092 and the signal line L12.

When the communication mode is the first mode, the first signal is output from the buffer 1091 and is input to the pad VOUT. The first signal is output to the signal line L11 via the pad VOUT1. When the communication mode is the second mode, the control clock is input from the signal line L11 to the pad VOUT1. The control clock is output the CDR circuit 104 via the pad VOUT1 and the switch SW1.

When the communication mode is the first mode, the second signal is output from the buffer 1092 and is input to the pad VOUT2. The second signal is output to the signal line L12 via the pad VOUT2.

Figure 11:
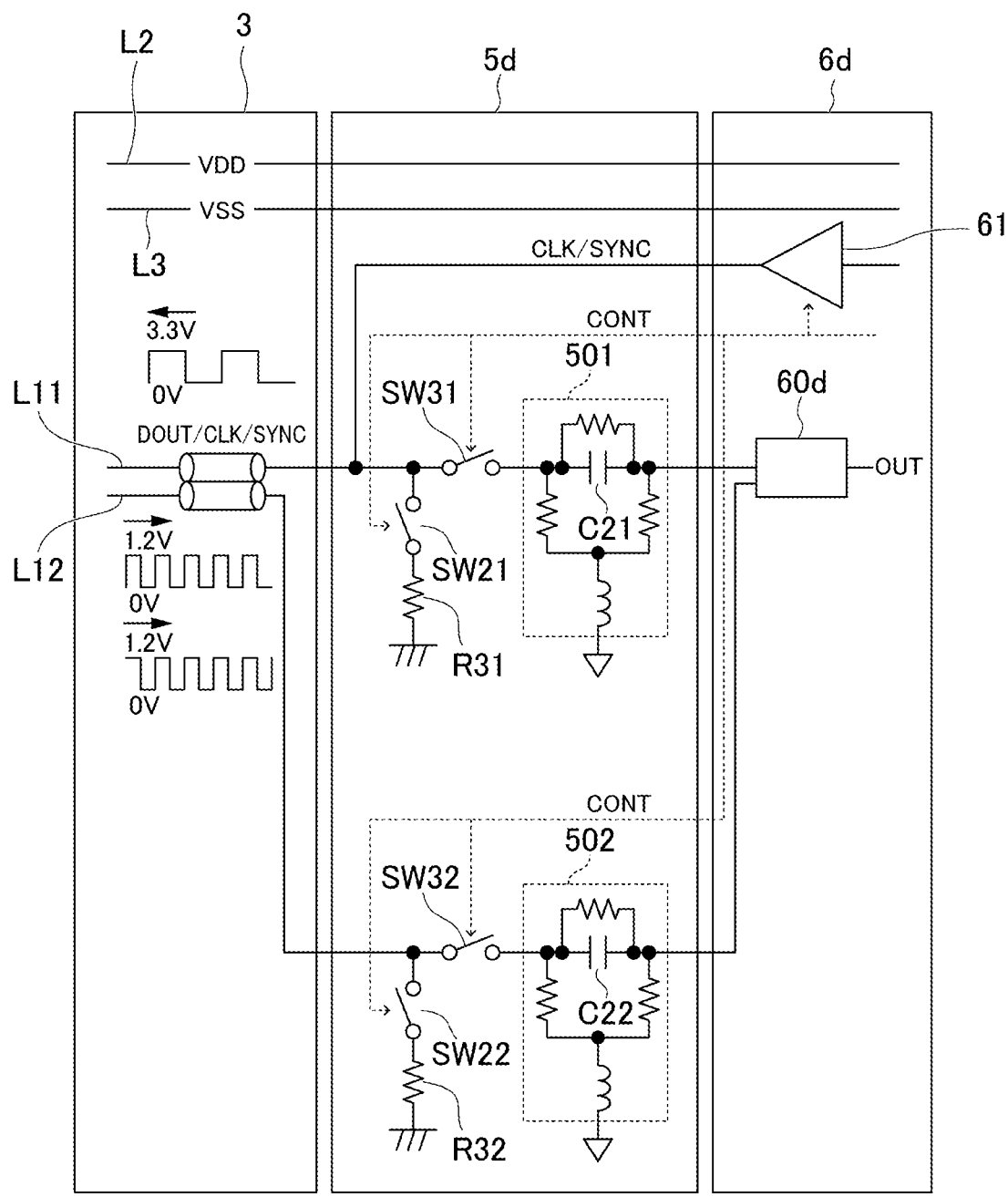
FIG. 11 is a block diagram showing a configuration of a connector unit and a processor included in the endoscope system according to the fourth embodiment of the present invention.

The connector unit 5 shown in FIG. 3 is changed to a connector unit 5d shown in FIG. 11, and the processor 6 shown in FIG. 3 is changed to a processor 6d shown in FIG. 11. FIG. 11 shows a configuration of the connector unit 5d and the processor 6d.

The connector unit 5d includes an equalizer 501, a switch SW21, a switch SW31, and a resistor R31. In addition, the connector unit 5d includes an equalizer 502, a switch SW22, a switch SW32, and a resistor R32. The processor 6d includes a video reception circuit 60d and a buffer 61.

The switch SW21 and the switch SW22 are similar to the switch SW2 shown in FIG. 3. The switch SW31 and the switch SW32 are similar to the switch SW3 shown in FIG. 3. The resistor R31 and the resistor R32 are similar to the resistor R3 shown in FIG. 3. The equalizer 501 and the equalizer 502 are similar to the equalizer 50 shown in FIG. 3.

When the communication mode is the first mode, the state of each of the switch SW21 and the switch SW22 becomes the ON state. At this time, the resistor R31 is electrically connected to the signal line L11, and the resistor R32 is electrically connected to the signal line L12. When the communication mode is the second mode, the state of each of the switch SW21 and the switch SW22 becomes the OFF state. At this time, the resistor R31 is electrically insulated from the signal line L11, and the resistor R32 is electrically insulated from the signal line L12. The state of each of the switch SW21 and the switch SW22 is controlled on the basis of the control signal CONT.

When the communication mode is the first mode, the state of each of the switch SW31 and the switch SW32 becomes the ON state. At this time, the equalizer 501 is electrically connected to the signal line L11, and the first signal is input to the equalizer 501. In addition, the equalizer 502 is electrically connected to the signal line L12, and the second signal is input to the equalizer 502. When the communication mode is the second mode, the state of each of the switch SW31 and the switch SW32 becomes the OFF state. At this time, the equalizer 501 is electrically insulated from the signal line L11, and the equalizer 502 is electrically insulated from the signal line L12. The state of each of the switch SW31 and the switch SW32 is controlled on the basis of the control signal CONT.

The equalizer 501 includes a capacitance element C21 and other elements. The equalizer 501 adjusts the frequency characteristics of the first signal. The equalizer 501 outputs the first signal of which the frequency characteristics are adjusted to the video reception circuit 60d. The equalizer 502 includes a capacitance element C22 and other elements. The equalizer 502 adjusts the frequency characteristics of the second signal. The equalizer 502 outputs the second signal of which the frequency characteristics are adjusted to the video reception circuit 60d.

When the communication mode is the first mode, the video reception circuit 60d receives the first signal and the second signal. The video reception circuit 60d includes a conversion circuit that restores the serial data by converting the first signal and the second signal constituting a differential signal into a single-ended signal. In addition, the video reception circuit 60d includes a decoding circuit that decodes the serial data encoded by the encoding circuit 108. In addition, the video reception circuit 60d includes deserializer that converts the decoded serial data into parallel data including a plurality of parallel bits. The video reception circuit 60d outputs the parallel data (OUT) to a circuit not shown in FIG. 11. When the communication mode is the second mode, the state of each of the switch SW31 and the switch SW32 is the OFF state. Therefore, the video reception circuit 60d stops reception of the first signal and the second signal.

The buffer 61 is similar to the buffer 61 shown in FIG. 3. The buffer 61 is electrically connected to the signal line L11. When the communication mode is the second mode, the buffer 61 outputs the control clock including the system clock and the imaging control signal to the signal line L11. When the communication mode is the second mode, the buffer 61 turns into the high-level state or the low-level state, thus outputting the control clock to the signal line L11. When the communication mode is the first mode, the buffer 61 turns into the high-impedance state. While the state of the buffer 61 is the high-impedance state, output of the control clock to the signal line L11 is stopped. The state of the buffer 61 is controlled on the basis of the control signal CONT.

The transmission cable 3 includes a plurality of cables. For example, the transmission cable 3 includes a first cable and a second cable. The signal line 11 and the power source line L2 are included in the first cable. For example, the signal line L11 is disposed on the core side of the first cable, and the power source line L2 is disposed on the outer side of the first cable. The signal line L12 and the power source line L3 are included in the second cable. For example, the signal line L12 is disposed on the core side of the second cable, and the power source line L3 is disposed on the outer side of the second cable. The signal line L11 and the power source line L3 may be included in the first cable, and the signal line L12 and the power source line L2 may be included in the second cable.

The ADC 106 and the serializer 107 may be changed to the ADC 106a shown in FIG. 5. The buffer 1091 or the buffer 1092 may be changed to the buffer 109a shown in FIG. 6. The control unit 12d does not need to include the voltage generation circuit 105 and may include the switch SW4, the inverter C1l, and the AND circuit AC1 shown in FIG. 7. The control unit 12d does not need to include the PLL 110, and the CDR circuit 104 may be changed to the CDR circuit 104c shown in FIG. 8.

In the fourth embodiment, the serial data are transmitted as a differential signal. The video reception circuit 60d can eliminate noise mixed into the differential signal passing through the transmission cable 3.

The camera unit 10d and the processor 6d are connected to each other by two cables. Therefore, it is possible to transmit the serial data as a differential signal without increasing the number of cables, compared to the first embodiment.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging system, comprising:
a camera unit; and
a control unit that is configured to operate on the basis of a system clock and is connected to the camera unit by a signal line that transmits serial data and the system clock,
wherein the camera unit comprises:
an imager configured to generate an analog video signal on the basis of a camera clock;
a video output circuit configured to convert the analog video signal into digital data and output the serial data including the digital data to the signal line on the basis of a serial clock having a higher frequency than a frequency of the camera clock;
a camera-clock generation circuit configured to generate the camera clock synchronized with the system clock output to the signal line; and
a serial-clock generation circuit configured to generate the serial clock synchronized with the system clock output to the signal line, and
the control unit comprises:
a video reception circuit that is electrically connected to the signal line and is configured to receive the serial data; and
a system-clock output circuit configured to output the system clock to the signal line in a blanking period during which output of the serial data to the signal line is stopped.

2. The imaging system according to claim 1,
wherein the video output circuit comprises:
an analog-to-digital conversion circuit configured to convert the analog video signal into the digital data including a plurality of parallel bits; and
a serializer that is configured to convert the digital data into the serial data and output the serial data to the signal line at a timing synchronized with the serial clock.

3. The imaging system according to claim 1,
wherein the video output circuit comprises an analog-to-digital conversion circuit that is configured to convert the analog video signal into the serial data and output the serial data to the signal line at a timing synchronized with the serial clock.

4. The imaging system according to claim 1,
wherein the camera-clock generation circuit is configured to generate the camera clock by dividing a frequency of the serial clock.

5. The imaging system according to claim 1,
wherein the serial data include two or more pieces of high level data and two or more pieces of low level data, and
the video output circuit comprises an encoding circuit configured to encode the serial data such that a sum of lengths of periods occupied by the two or more pieces of high level data output to the signal line is almost the same as a sum of lengths of periods occupied by the two or more pieces of low level data output to the signal line.

6. The imaging system according to claim 1,
wherein the video output circuit comprises a three-state buffer configured to turn into any one of a high-level state, a low-level state, and a high-impedance state,
a state of the three-state buffer switches between the high-level state, the low-level state, and the high-impedance state, and
the three-state buffer is configured to output the serial data to the signal line by turning into the high-level state or the low-level state and turn into the high-impedance state in the blanking period.

7. The imaging system according to claim 1,
wherein the system-clock output circuit is configured to output the system clock including a negative voltage to the signal line, and
the camera unit further comprises a capacitor that is configured to hold the negative voltage and output the negative voltage to the imager.

8. The imaging system according to claim 7,
wherein the system-clock output circuit is configured to output the system clock alternately including a positive voltage and the negative voltage to the signal line, and
the camera unit further comprises:
a switch that is capable of switching between an ON state and an OFF state and is electrically connected to the signal line and the capacitor; and
a control circuit configured to set a state of the switch to the ON state when the negative voltage is output to the signal line and set the state of the switch to the OFF state when the positive voltage is output to the signal line.

9. The imaging system according to claim 7,
wherein the system-clock output circuit is configured to output the system clock including the negative voltage lower than a design voltage designed for the imager such that the negative voltage input to the capacitor almost matches the design voltage.

10. An endoscope connected to a control unit by a signal line that transmits serial data and a system clock, the endoscope comprising:
an imager configured to generate an analog video signal on the basis of a camera clock;
a video output circuit configured to convert the analog video signal into digital data and output the serial data including the digital data to the signal line on the basis of a serial clock having a higher frequency than a frequency of the camera clock;
a camera-clock generation circuit configured to generate the camera clock synchronized with the system clock output to the signal line in a blanking period during which output of the serial data to the signal line is stopped; and
a serial-clock generation circuit configured to generate the serial clock synchronized with the system clock output to the signal line.

* * * * *